United States Patent

Yamamoto et al.

[11] Patent Number: 5,643,174
[45] Date of Patent: Jul. 1, 1997

[54] ENDOSCOPIC GUIDE TUBE WITH EMBEDDED COIL SPRING

[75] Inventors: Manabu Yamamoto, Tokyo; Zenetu Suzuki; Yasunobu Izumi, both of Akita, all of Japan

[73] Assignee: Sumitomo Bakelite Company Limited, Tokyo, Japan

[21] Appl. No.: 286,199

[22] Filed: Aug. 8, 1994

[30] Foreign Application Priority Data

Aug. 18, 1993 [JP] Japan .................. 5-204279
Dec. 15, 1993 [JP] Japan .................. 5-314754

[51] Int. Cl.⁶ .................................................. A61B 1/04
[52] U.S. Cl. .................... 600/114; 600/120; 600/194
[58] Field of Search ............................ 600/114, 120, 600/194, 195; 128/207.14, 200.26; 604/264, 282

[56] References Cited

U.S. PATENT DOCUMENTS

| | | | |
|---|---|---|---|
| 2,693,182 | 11/1954 | Phillips | 128/200.26 |
| 3,913,565 | 10/1975 | Kawahara | 600/114 |
| 4,066,071 | 1/1978 | Nagel | 600/114 |
| 4,068,658 | 1/1978 | Berman | 128/208 |
| 4,195,624 | 4/1980 | Douglas | 600/114 |
| 4,332,242 | 6/1982 | Chikama | 600/114 |
| 4,630,649 | 12/1986 | Oku | 600/114 |
| 4,640,273 | 2/1987 | Green et al. | 128/207.14 |
| 4,737,153 | 4/1988 | Shimamura et al. | 604/282 |
| 4,807,593 | 2/1989 | Ito | 600/114 |
| 4,825,861 | 5/1989 | Koss | 128/200.26 |
| 4,990,143 | 2/1991 | Sheridan | 604/282 |
| 5,273,545 | 12/1993 | Hunt et al. | 604/264 |
| 5,303,697 | 4/1994 | Brain | 128/200.26 |
| 5,423,848 | 6/1995 | Washizuka et al. | 604/264 |

*Primary Examiner*—Linda C. Dvorak
*Assistant Examiner*—Beverly M. Flanagan
*Attorney, Agent, or Firm*—Browdy and Neimark

[57] ABSTRACT

A guide tube comprising a tube body having a throughhole penetrated therethrough in the axial direction and a mouthpiece provided at the rearward end of the tube body, or comprising a tube body having a throughhole penetrated therethrough in the axial direction, a connector provided at the rearward end of the tube body and a mouthpiece engageable with and detachable from the connector, the tube body being embedded with a coil spring in the tube wall and cut slantly to the axial direction at the forward end, and the mouthpiece having a circular or elliptical cross-sectional shape, a rib at the forward end and a flange at the rearward end, and the connector being in a structure engageable with and detachable from the mouthpiece and having at the rearward end a sealing film member with a slit or a perforation at the center facilitates passage of an endoscope through the phalynx to the esophagus, simplifies washing of or aspiration from the esophagus or stomach and shortens the treating time and reduces a painful burden on patients much more, when the engageable and detachable mouthpiece is used.

20 Claims, 5 Drawing Sheets

5,643,174

ENDOSCOPIC GUIDE TUBE WITH EMBEDDED COIL SPRING

BACKGROUND OF THE INVENTION

1) Field of the Invention

The present invention relates to an instrument for inserting an endoscope through the pharynx for the medical treatment.

2) Related Prior Art

An endoscope has been widely used to diagnose and treat tumors in the stomach, esophagus, etc. or lesions such as varices in the alimentary tract. However, the endoscope now in practical use has an outer diameter as large as about 10 mm, and thus operators' skill is required for the insertion of an endoscope with a large painful burden on the patients. Furthermore, the endoscope must be repeatedly inserted and withdrawn, depending on the required medical treatment, resulting in further increase in the burden on the patients.

On the other hand, a guide tube, as shown in FIG. 8A, is now commercially available to facilitate the insertion of an endoscope, thereby improving the operability and decreasing the burden on the patients. The guide tube comprises a tube body 21 of soft plastic resin and a mouthpiece 23 having a flange 24 at the rearward end.

The guide tube is used as follows:

At first, an endoscope is inserted through the throughhole of the guide tube and set thereto. Then, only the endoscope is moved forward through the throughhole of the guide tube and inserted from the oral cavity through the pharynx to make the forward end of the endoscope reach the esophagus. Then, the guide tube is slided down along the endoscope to insert the forward end of the guide tube into the pharynx region. Usually, the lumen of the pharynx region is bent and it is most difficult in the insertion of an endoscope to pass the endoscope through the pharynx region. By retaining the guide tube in the pharynx region, the successive insertion and withdrawing of the endoscope can be facilitated.

As materials for the tube body 21, mainly soft plastic resins such as polyvinyl chloride, etc. are used. The mouthpiece 23 serves to fix the guide tube by holding it between teeth of a patient after the guide tube has been inserted to the pharynx region. Thus, rigid or hard plastic resins are used as materials for the mouthpiece 23.

An example of practically using the guide tube for facilitated passage of an endoscope through the pharynx region is ligation of esophagal varices.

The ligation of esophagal varices is carried out as follows:

As shown in FIG. 8B, an endoscope 22 provided with a cylindrical device 26 at the forward end is inserted into the esophagus through the guide tube to make the device 26 reach a varix. The varix is sucked into the device 26, and then an elastic O ring expanded and mounted around the outer periphery of the inner tube of the device 26 is released from the forward end of the inner tube of the device 26 by pulling back a wire inserted through a forceps channel of the endoscope and fixed to the inner tube, thereby fixing the elastic O ring around the basis of the sucked polyp-like varix. That is, the varix is mechanically ligated by the contracting force of the elastic O ring to strangulate and slough off the ligated varix. The endoscope must be inserted and withdrawn for one ligation, and thus the guide tube is used for facilitating the repeated passage of the endoscope through the pharynx region (see U.S. Pat. No. 4,735,194 and a catalog of Stiegman-Golf Endoscopic Ligator, made by C. R. Bard, Inc, U.S.A. and distributed in Japan by K. K. Medicon, Japan).

However, the conventional guide tube, as shown in FIG. 8B has such a problem that, when the guide tube is bent, the tube body 21 is squashed at the bend 25 to narrow the throughhole, as shown in FIG. 8B, and thus when the guide tube is inserted to the pharynx region, the guide tube is bent in the pharynx region, deteriorating the smooth passage of an endoscope therethrough.

To solve the problem, the throughhole of the guide tube must be broadened. That is, the guide tube has a larger outer diameter than the necessary one, resulting in a further increase in the burden on the patients. Furthermore, in the case of bleeding from the esophagus, the blood is washed with water or physiological saline and discharged from the esophagus by aspiration. In the case of aspiration, there is such a problem that air leaks in through the guide tube, making the aspiration force insufficient, or when air is blown into the esophagus to broaden the endoscopic sight within the esophagus on the other hand, the blown air leaks out through the guide tube, resulting in a failure to sufficiently broaden the endoscopic sight.

In the case of inserting an endoscope into the pharynx region, patients often bite the endoscope due to patients' high tension, causing an endoscope trouble or disorder. To solve the problem, a patient is allowed to hold a mouthpiece 27 between teeth, as shown in FIG. 9A, and an endoscope 22 is inserted into the patient's pharynx region 20 through the throughhole of the mouthpiece 27. However, in the case of the mouthpiece of such a conventional type as shown in FIG. 9A, the endoscope is sometimes to be removed after one medical treatment, and the endoscope must be again inserted for a successive medical treatment through the mouthpiece, whereby the treating time is so prolonged as to give pains to the patient. Furthermore, it is quite difficult to insert a guide tube through the throughhole of the mouthpiece held between the teeth, and thus the mouthpiece of conventional type is not practically applicable to the guide tube.

SUMMARY OF THE INVENTION

An object of the present invention is to provide an improved guide tube that can overcome poor passage of an endoscope through the conventional guide tube, particularly, in the pharynx region and can also overcome air leakage through the guide tube.

It will be seen in FIG. 5A that the engagement of the connector 8 to the mouthpiece 3 involves an angular alignment of these parts, because the engaging system or coupling mechanisms require that these parts be angularly aligned prior to assembly.

Another object of the present invention is to provide an improved guide tube that can facilitate the passage of an endoscope through the phalynx region and can also simplify washing of esophagus and aspiration of the washing liquid therefrom, thereby shortening the treating time and reducing a painful burden on patients.

Other object of the present invention is to provide an improved guide tube that can further shorten the treating time and reduce the painful burden on patients by use of an engageable and detachable mouthpiece.

According to one aspect of the present invention there is provided an instrument for inserting an endoscope into the esophagus, that is, a guide tube, which comprises a tube body having a throughhole penetrated therethrough in the axial direction and a mouthpiece provided at the rearward end of the tube body, the tube body being embedded with a coil spring in the tube wall and cut slantly to the axial direction at the forward end, and the mouthpiece having a circular or elliptical cross-sectional shape, a rib at the forward end and a flange at the rearward end, and the flange having a sealing film member with a slit or a perforation at the center.

According to a second aspect of the present invention there is provided an instrument for inserting an endoscope into the esophagus, that is, a guide tube, which comprises a tube body having a throughhole penetrated therethrough in the axial direction, a connector provided at the rearward end of the tube body and a mouthpiece and engageable with and detachable from the connector, the tube body being embedded with a coil spring in the tube wall and cut slantly to the axial direction at the forward end, and the mouthpiece having a circular or elliptical cross-sectional shape, a rib at the forward end and a flange at the rearward end, and the connector being in a structure engageable with and detachable from the mouthpiece and having at the rearward end a sealing film member with a slit or a perforation at the center.

BRIEF DESCRIPTION OF THE INVENTION

FIGS. 2A and 2B are schematic views showing the structure of a guide tube according to one embodiment of the second aspect of the present invention, wherein FIG. 2A is a side view of the guide tube with the mouthpiece engaged with the connector and FIG. 2B is a cross-sectional view showing the guide tube with a mouthpiece detached from a connector.

FIG. 8A is a side view of the conventional guide tube and FIG. 8B is a view showing the problem of the conventional guide tube.

FIG. 9A is a perspective view of the conventional mouthpiece and FIG. 9B is a view showing an application of the conventional mouthpiece.

PREFERRED EMBODIMENTS OF THE INVENTION

Figure 1:
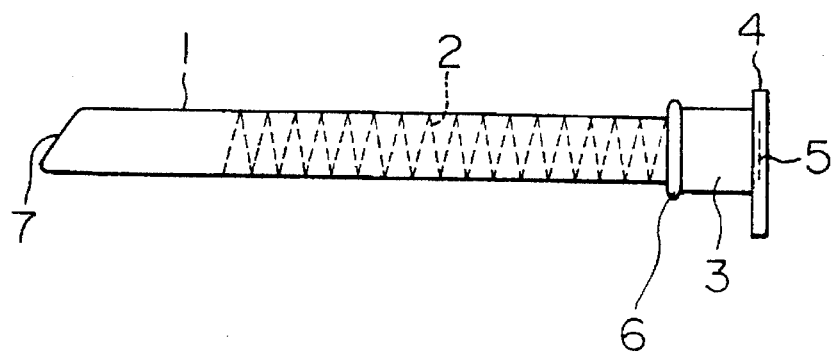
FIG. 1 is a schematic view showing the structure of a guide tube according to one embodiment of the first aspect of the present invention.

The present invention will be described in detail below, referring to the drawings.

FIG. 1 schematically shows the structure of a guide tube according to one embodiment of the first aspect of the present invention.

A guide tube according to the first aspect of the present invention comprises a tube body 1 having a throughhole penetrated therethrough in the axial direction and a mouthpiece 3 provided at the rearward end of the tube body 1, the tube body 1 being embedded with a coil spring 2 in the tube wall and cut slantly to the axial direction at the forward end 7, and the mouthpiece 3 having a circular or elliptical cross-section perpendicular to the axial direction of the tube body 1, a rib 6 at the forward end and a flange 4 at the rearward end, and the flange 4 having a sealing film member 5 with a slit or a perforation at the center so as to close the throughhole of the mouthpiece 3.

Figure 2A:
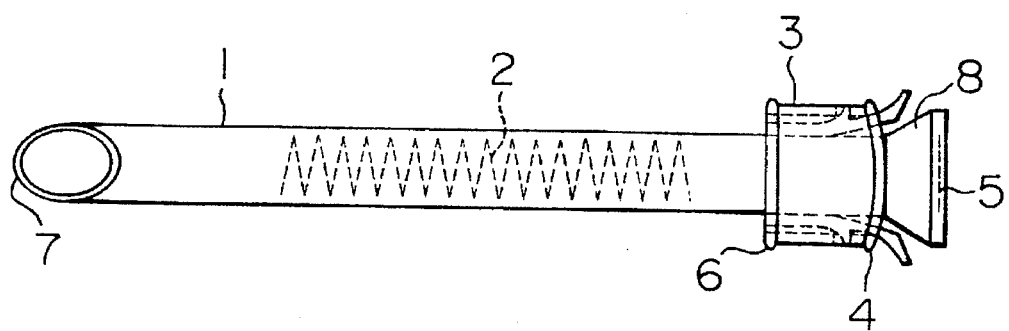
Figure 2B:
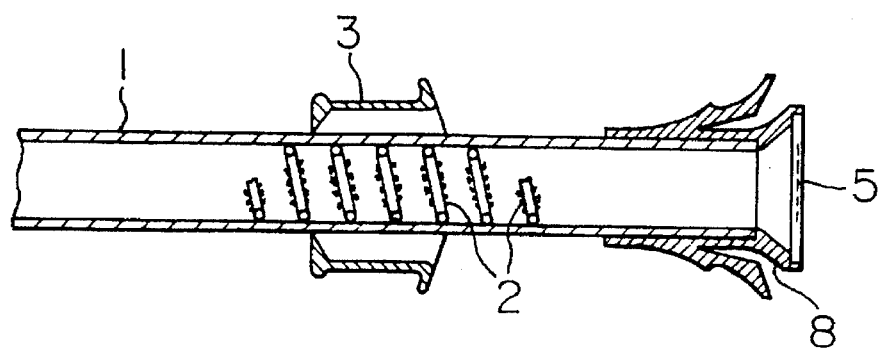

FIGS. 2A and 2B schematically show the structure of a guide tube according to one embodiment of the second aspect of the present invention, where FIG. 2A is a side view of the guide tube and FIG. 2B is a view showing the guide tube with a mouthpiece detached from a connector.

A guide tube according to the second aspect of the present invention comprises a tube body 1 having a throughhole penetrated therethrough in the axial direction, a connector 8 provided at the rearward end of the tube body 1 and a mouthpiece 3 engageable with and detachable from the connector 8, the tube body 1 being embedded with a coil spring 2 in the tube wall and cut slantly to the axial direction at the forward end 7. The connector 8 is tapered to make the inner diameter larger rearwardly, and has at the rearward end a sealing film member 5 with a slit or a perforation at the center so as to close the throughhole of the connector 8. The mouthpiece 3 has a circular or elliptical cross-sectional shape, a rib 6 at the forward end and a flange 4 at the rearward end, and is engaged with the tube body 1 through the throughhole of the mouthpiece 3 by putting the mouthpiece 3 along the tube body 1 from the forward end 7 of the tube body 1, as shown in FIG. 2B, and is engageable with and detachable from the connector 8.

As materials for the tube body 1, it is preferable to use soft plastic resins, for example, polyvinyl chloride resin, polyurethane resin, and rubber resin. To prevent damages of cavity or lumen wall, when the guide tube is inserted into the oral cavity or the pharynx, it is thus preferable to use plastic resins as soft as possible.

The size of the tube body 1 depends on the outer diameter of an endoscope to be inserted therethrough, and the inner diameter of the tube body 1 usually is by about 2–about 10 mm larger than the outer diameter of the endoscope. The wall thickness of the tube body 1 depends on the species of plastic resins and material of coil spring embedded in the tube wall. The thinner the tube wall, less pains on patients. Thus, it is preferable that the wall thickness is about 1.0–about 3.00 mm.

Coil spring 2 embedded in the tube wall of tube body 1 is a coiled wire of metal or rigid plastic resin having a force sufficient to prevent the throughhole of the tube body 1 from squashing when the tube body 1 is bent. Coiled wire of metal includes, for example, spring wires of stainless steel such as SUS 304, etc., but is not limited thereto. Coiled wire of rigid plastic resin includes, for example, spring wires of polyamide, fluorohydrocarbon resin, etc. and is not particularly limited thereto, so long as it has a resistance to heating when it is to be embedded into the pipe wall of tube body 1 and also a rigidity sufficient to maintain the strength of tube body 1.

Since the guide tube is to be retained at the bend site of the phalynx region, it is appropriate that the tube body 1 is 100–300 mm long in the case of EVL (endoscopic variceal ligation) and can be as long as 300–500 mm in the case of EIS (endoscopic esophagal varix sclerosis treatment). The region of the tube body 1 necessary for embedding the coil spring 2 therein ranges from a point at 45±10 mm to a point at 200±30 mm, as measured from the position of flange 4 in the case of the first aspect of the present invention or from the position of the rearward end of the connector 8 in the case of the second aspect of the present invention, that is, is in a range of 145–195 mm as a maximum length, which can fully cover the central site corresponding to the pharynx region of a patient when the guide tube is retained there. The longer the region, the less flexible the tube body. When the region is too short, no satisfactory effect will be obtainable. Thus, it is preferable that the region, that is, the coil spring 2, is about 120–about 160 mm.

The coil spring 2 can be embedded into the tube body 1 just from the position of rib 6 at the forward end of the mouthpiece 3 in the case of the first aspect of the present invention or just from the position of the mouthpiece rib 6 when the mouthpiece 3 is engaged with the connector 8 in the case of the second aspect of the present invention, but it is preferable to provide a region without the embedded spring coil to such a distance from the rib 6 as mentioned above, thereby giving a natural fitness to the guide tube when a patient holds it between teeth.

To improve the insertability of the guide tube and prevent the forward end of the endoscope from being caught when the endoscope is withdrawn, the tube body 1 is slantly cut at the forward end 7, that is, at a cut angle of 40°–70°, preferably 50°–60°, to the axial direction of the tube body 1.

Mouthpiece 3 for use in the first and second aspects of the present invention is a molding of plastic resin or rigid rubber usually used in the medical treatment, and the mouthpiece materials are not particularly limited, so long as the mouthpiece material can satisfy such requirements as being hard to break and easy to mold. It is desirable that the mouthpiece material is soft and gives no strange feeling to a patient when he holds the mouthpiece between teeth. The flange 4 and the rib 6 of the mouthpiece 3 serve to stabilize the state of holding it between teeth and also to improve the resistance to the biting force. Thus, the length, width and thickness are selected in view of the material quality, rigidity, the wall thickness of tube body 1, etc.

Figure 3A:
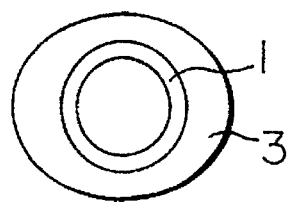
FIGS. 3A and 3B are views showing embodiments of cross-sectional shape of a mouthpiece according to the first aspect of the present guide tube or a connector according to the second aspect of the present guide tube.
Figure 3B:
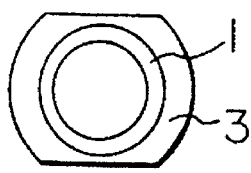

Furthermore, it is preferable from the viewpoint of strong biting force on the mouthpiece by a patient that the trunk and the rib 6 of the mouthpiece 3 have an elliptical shape, as shown in FIG. 3A or an elliptical shape having a flat top side and a flat bottom side for easier holding between teeth, as shown in FIG. 3B. Furthermore, the flange 4 of the mouthpiece 3 has an ellipsoidal shape with a flat top side as shown in FIGS. 4A, 4B and 4C or both flat top side and bottom side or a narrower vertical span than the horizontal span so as not to prevent the flange 4 from contact with the nose when a patient holds the mouthpiece between teeth.

Connector 8 provided at the rearward end of the tube body 1 according to the second aspect of the present invention is a molding of plastic resin or rigid rubber usually used in the medical treatment, and the connector materials are not particularly limited thereto, so long as the connector materials can satisfy such requirements as being hard to break and easy to mold. To facilitate engagement with or detachment from the mouthpiece 3, the connector materials must have a sufficient slidability to the mouthpiece without any adhesion to the mouthpiece and also must be less torn, because hinges are sometimes integrally formed from the side surface of the connector as a lock mechanism when the mouthpiece 3 is mounted onto the connector 8.

Furthermore, it is preferable from the viewpoint of engagement with or detachment from the mouthpiece 3 that the connector 8 has a cylindrical shape. In view of the insertability of an endoscope, etc., the connector is tapered broader toward the rearward end, that is, to smoothly broaden the inner diameter without any level difference from the inner diameter of the tube body 1 at the junction with the tube body 1 to prevent the endoscope from being caught at the junction.

Figure 4A:
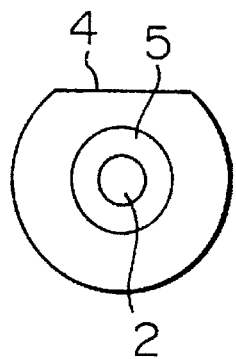
FIGS. 4A, 4B and 4C are views showing embodiments of perforation, slit and cross slit, respectively, through the sealing film member provided at the rearward end of a mouthpiece according to the first aspect of the present guide tube or a connector according to the second aspect of the present guide tube.
Figure 4B:
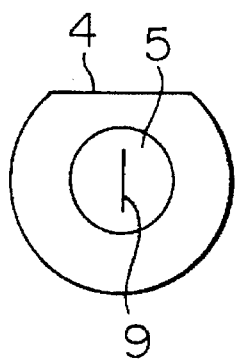
Figure 4C:
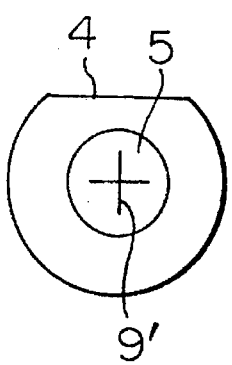

Sealing film member 5 provided at the rearward end of the flange 4 according to the first aspect of the present invention or at the rearward end of the connector 8 according to the second aspect of the present invention is an elastic plastic resin or rubber sheet with a perforation 8 as shown in FIG. 4A, or a slit 9 as shown in FIG. 4B, or a cross slit 9' as shown in FIG. 4C, and covers and seals the rearward end of the tube body 1. When an endoscope is inserted through the perforation 8, slit 9 or cross slit 9', the peripheral end of perforation 8 or the ends of slit 9 or cross slit 9' of the sealing film member 5 gives tight fitting to the outer periphery of the endoscope to ensure complete sealing between the guide tube and the endoscope.

Figure 5A:
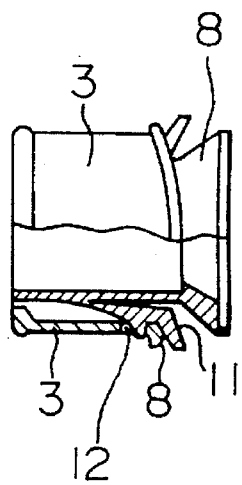
FIGS. 5A, 5B and 5C are views showing mounting a mouthpiece onto a connector according to the second aspect of the present guide tube.
Figure 5B:
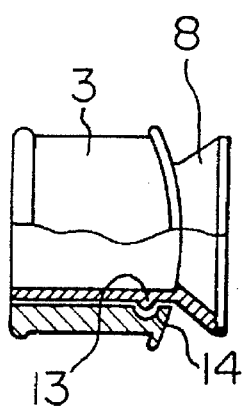
Figure 5C:
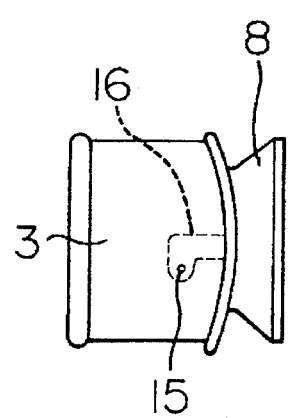

The mouthpiece 3 can be engaged with the connector 8 according to the second aspect of the present invention, for example, by a spring system as shown in FIG. 5A, i.e. by engaging two projections provided each on a pair of vanes 11 on the side surface of connector 8 with two holes 12 provided on the mouthpiece 3 and near the flange 4, or by a rib system, as shown in FIG. 5B, i.e. by engaging a rib 13 provided at the outer periphery of connector 8 and near the rearward end thereof with a groove 14 provided on the inner periphery of mouthpiece 3 and at the rearward end thereof, or by a rock system, as shown in FIG. 5C, i.e. by engaging a projection 15 provided on the outer periphery of connector 8 and near the rearward end thereof with an L-shaped groove 16 provided on the inner periphery of the mouthpiece 3 and at the rearward end thereof, and turning the connector 8 to fix the mouthpiece 3 to the connector 8. The engaging system is not particularly limited thereto, but since the guide tube is sometimes inserted into the oral cavity by slightly turning the guide tube, the spring system, as shown in FIG. 5A, is preferable.

Guide tube according to the first aspect of the present invention can be inserted into the phalynx region in the following manner.

Figure 6:
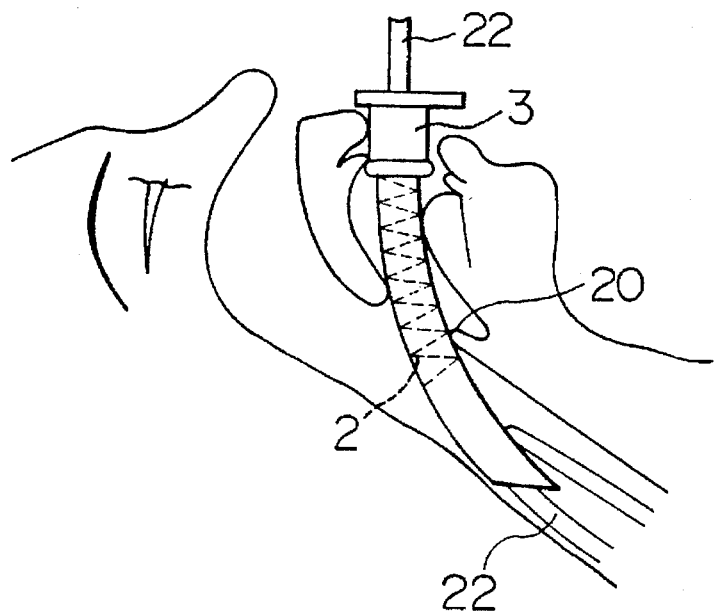
FIG. 6 is a view showing a state of inserting a guide tube according to the first aspect of the present guide tube into the phalynx region of a patient and retaining it there.

As shown in FIG. 6, the outer periphery of a fiber of endoscope 22 is coated with Xylocaine jerry (trademark of lidocaine jelly), etc. and the endoscope 22 is inserted into a guide tube and set thereto. At first, only the endoscope is inserted into the phalynx region of a patient to allow its forward end to reach the region. Then, the guide tube is slided down along the inserted endoscope 22 and inserted into the phalynx region. When the guide tube is completely inserted so that the rearward end of the guide tube can be approached to the mouth lips as shown in FIG. 6, the mouthpiece 3 is held between the teeth and its position is fixed to retain the guide pipe in the phalynx region. Then, the endoscope 22 is further inserted to a target site.

Guide tube according to the second aspect of the present invention can be inserted into the phalynx region in the following manner.

Figure 7:
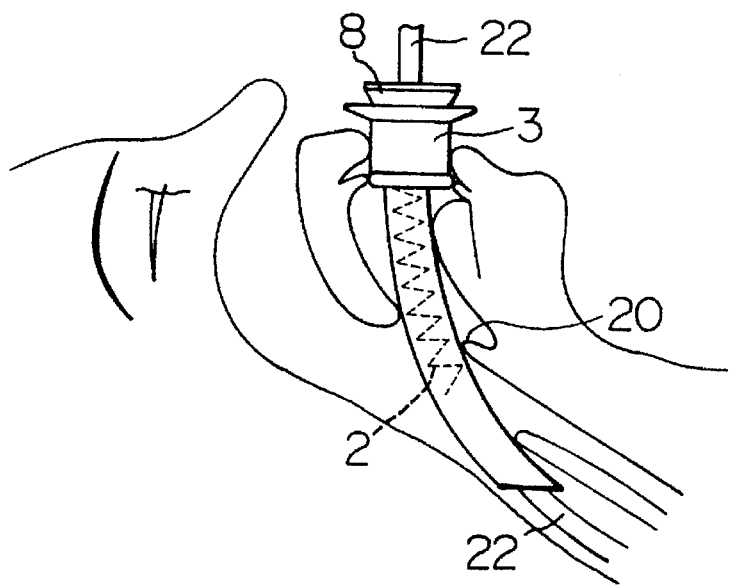
FIG. 7 is a view showing a state of inserting a guide tube according to the second aspect of the present guide tube into the phalynx region of a patient and retaining it there.
Figure 8A:
FIG. 8A and 8B are views showing the conventional guide tube, where
Figure 8B:
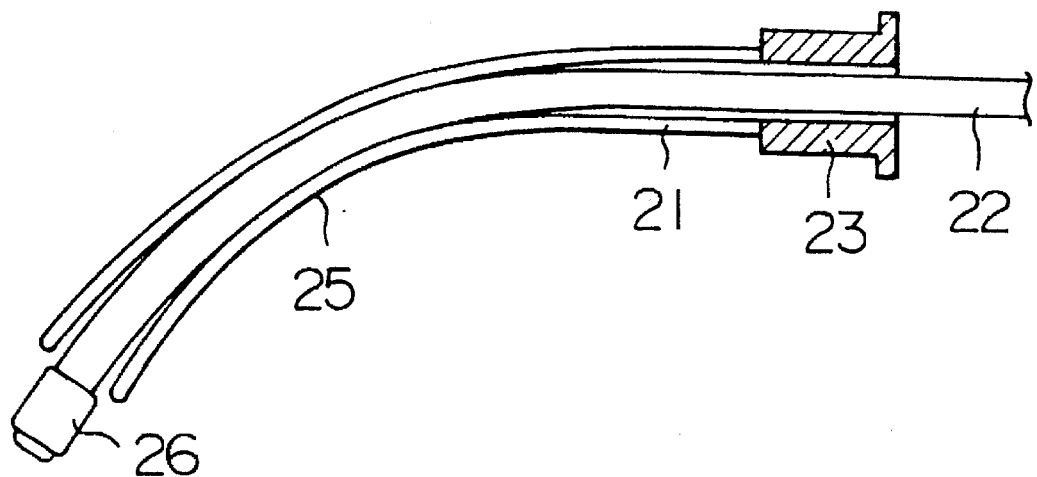
Figure 9A:
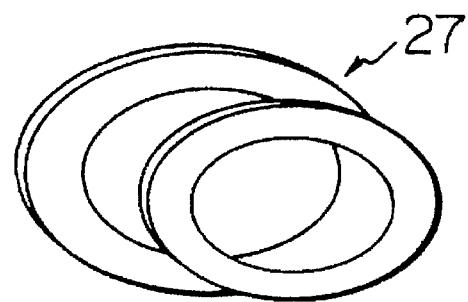
FIGS. 9A and 9B are views showing the conventional mouthpiece, where
Figure 9B:
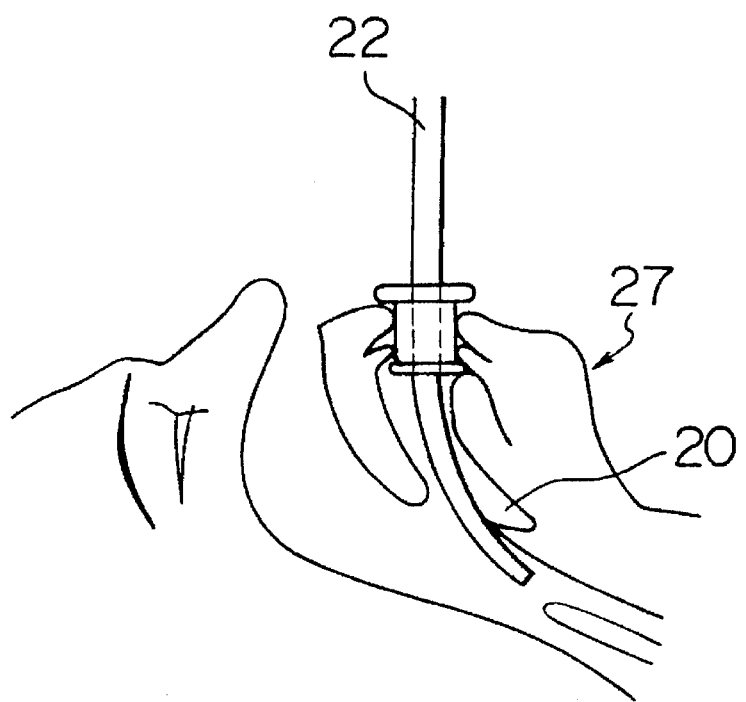

As shown in FIG. 7, the outer periphery of a fiber of endoscope 22 is coated with Xylocaine jelly (trademark of lidocaine jelly), etc. and the endoscope 22 is set into the throughhole of guide tube through connector 8 provided at the rearward end of the guide tube. Then, mouthpiece 3 is held between the teeth of a patient and, if necessary, fixed to the mouth lips by a rubber band or tape. At first, the endoscope 22 is inserted through the mouthpiece 3 into the phalynx region of the patient to allow its forward end to reach the region. Then, the guide tube is slided down along the inserted endoscope 22 through the mouthpiece 3 and inserted into the phalynx region, as shown in FIG. 7. Then, the connector 8 at the rearward end of the guide tube is engaged with the mouthpiece 3 to fix it to the mouthpiece 3 and retain the guide tube in the phalynx region. Then, the endoscope 22 is further inserted to a target site.

It is desirable that the middle position of coil spring 2 embedded in the tube wall of guide tube is located in the phalynx region 20. Thus, a guide tube having an appropriate length must be used upon selection from guide tubes of various lengths in view of the age and body structure of a patient undergoing a medical treatment. When the guide tube is retained in the flexible site such as the phalynx region, etc. in this manner, the guide tube can be prevented from squashing, while keeping the throughhole so open as to permit very smooth insertion or drawing of an endoscope 22 due to the squashing-preventing force of spring coil 2 embedded in the tube wall.

According to the present guide tube for inserting an endoscope the endoscope can be smoothly inserted or withdrawn without squashing and the consequent closure of the throughhole of the guide tube even if the guide tube is bent. Furthermore, by providing a sealing film member at the rearward end of the guide tube, sufficient and effective aspiration and air blowing can be attained without any air leakage when the esophagus or stomach is washed, improving the operability and shortening the treating time.

Thus, the present invention provides an effective instrument for inserting an endoscope.

According to the second aspect of the present invention, a guide tube can be inserted while holding a mouthpiece between the teeth of a patient the operability can be further improved and the treating time can be also further shortened. Thus, the present invention provides a more effective instrument for inserting an endoscope.

What is claimed is:

1. A guide tube for an endoscope, the guide tube comprising:
   a tube body having a throughhole penetrated therethrough in an axial direction and a mouthpiece provided at a rearward end of the tube body, the tube body including a tube wall and an inner surface; and
   a coil spring substantially completely embedded in the tube wall such that individual coils are surrounded by tube wall material and the inner surface is substantially smooth so as to prevent catching of the endoscope as it passes;
   the tube body being cut at a slant to the axial direction at a forward end;
   the mouthpiece having one of a circular cross-sectional shape and an elliptical cross-sectional shape, and including a rib at the forward end and a flange at the rearward end, the flange including a sealing film member with a slit or a perforation at the center.

2. A guide tube according to claim 1, wherein the coil spring is embedded in the tube wall in a region from a position of at least 35 mm to a position of maximum 230 mm, as measured from the flange at the rearward end of the mouthpiece.

3. A guide tube according to claim 1, wherein the tube body is cut at the forward end at an angle of 40° to 70° to the axial direction of the tube body.

4. A guide tube according to claim 1, wherein the flange has a flat top side or both flat top side and flat bottom side, or a narrower vertical span than the horizontal span.

5. The guide tube according to claim 1, wherein the coil spring comprises generally a single helix.

6. The guide tube according to claim 1, wherein the coil spring has a wire diameter greater than 1.0 millimeter.

7. The guide tube according to claim 1, wherein the coil spring has a wire diameter substantially equal to a tube wall thickness of the tube wall.

8. The guide tube according to claim 1, wherein coil turns of the coil spring are separated by an axial distance substantially greater than a tube wall thickness of the tube wall.

9. A guide tube for an endoscope, the guide tube comprising:
   a tube body including a tube wall and an inner surface and having a throughhole penetrated therethrough in an axial direction;
   a connector fixed to a rearward end of the tube body; and
   a slidable mouthpiece engageable with and detachable from the connector and slidable on the tube body when detached from the connector;
   a coil spring substantially completely embedded in the tube wall such that individual coils are surrounded by tube wall material and the inner surface is substantially smooth so as to prevent catching of the endoscope as it passes;
   the tube body being cut at a slant to the axial direction at a forward end;
   the mouthpiece including a rib at the forward end and a flange at the rearward end, and
   the connector being engageable with and detachable from the mouthpiece and including at the rearward end a sealing film member with a slit or a perforation at the center.

10. A guide tube according to claim 9, wherein the coil spring is embedded in the tube wall in a region from a position of at least 35 mm to a position of maximum 230 mm, as measured from the rearward end of the connector.

11. A guide tube according to claim 9, wherein the tube body is cut at the forward end at an angle of 40° to 70° to the axial direction of the tube body.

12. A guide tube according to claim 9, wherein the flange has a flat top side or both flat top side and flat bottom side, or a narrower vertical span than the horizontal span.

13. The guide tube according to claim 9, wherein the mouthpiece has a circular cross-sectional shape.

14. The guide tube according to claim 13, comprising a snap-in coupling mechanism for engaging the mouthpiece with the connector when the mouthpiece is slid over the tube body onto the connector.

15. The guide tube according to claim 9, wherein the mouthpiece has an elliptical cross-sectional shape.

16. The guide tube according to claim 15, comprising a snap-in coupling mechanism for engaging the mouthpiece with the connector when the mouthpiece is slid over the tube body onto the connector.

17. The guide tube according to claim 16, wherein the snap-in coupling mechanism angularly aligns the mouthpiece to the connector about the axial direction.

18. The guide tube according to claim 9, wherein the coil spring comprises generally a single helix and has a wire diameter greater than 1.0 millimeter.

19. The guide tube according to claim 9, wherein the coil spring has a wire diameter substantially equal to a tube wall thickness of the tube wall.

20. The guide tube according to claim 9, wherein coil turns of the coil spring are separated by an axial distance substantially greater than a tube wall thickness of the tube wall.

* * * * *